US00PP10565P

United States Patent [19]

Meilland

[11] Patent Number: Plant 10,565

[45] Date of Patent: Aug. 25, 1998

[54] HYBRID TEA ROSE PLANT NAMED 'MEIPAROS'

[75] Inventor: Alain A. Meilland, Antibes, France

[73] Assignee: The Conard-Pyle Company, West Grove, Pa.

[21] Appl. No.: 796,905

[22] Filed: Feb. 6, 1997

[51] Int. Cl.[6] ..... A01H 5/00

[52] U.S. Cl. ..... Plt./18

[58] Field of Search ..... Plt./18, 19

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive fragrant pink blossoms. The fragrance of the blooms is pronounced and is stable and is well maintained even when the blossoms are cut and placed in a vase. Such blossoms are long-lasting and exhibit a good petal-drop propensity. The plant exhibits dark green and glossy foliage, as well as good disease resistance. The new variety is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Tanselbon' variety (non-patented in the United States). The male parent (i.e., the pollen parent) was the 'Meiborfil' variety (non- patented in the United States). The parentage of the new variety can be summarized as follows:

'Tanselbon'×'Meiborfil'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms attractive long-lasting fragrant pink blossoms,
(b) exhibits a vigorous erect growth habit,
(c) forms attractive dark green and glossy foliage,
(d) exhibits good disease resistance, and
(e) is particularly well suited for cut flower production under greenhouse growing conditions.

The new variety well meets the needs of the horticultural industry and is particularly well suited for the commercial production of cut flowers while growing indoors. The fragrance is pronounced and is stable and is well retained even when the blossoms are cut and are present in a vase.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meiparos' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower — plan view — obverse;

FIG. 7—illustrates a specimen of an open flower — plan view — reverse;

FIG. 8—illustrates a specimen of a fully open flower — plan view— obverse;

FIG. 9—illustrates a specimen of a fully open flower — plan view— reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets — plan view — upper surface;

FIG. 15—illustrates a specimen of a leaf with five leaflets — plan view — under surface; and FIG. 16—illustrates a specimen of a leaf with seven leaflets — plan view — upper surface.

DETAILED DESCRIPTION

Figures 1, 2, 3, 4, 5, 6, 7, 8, 9, 10, 11, 12, 13, 14, 15, 16:
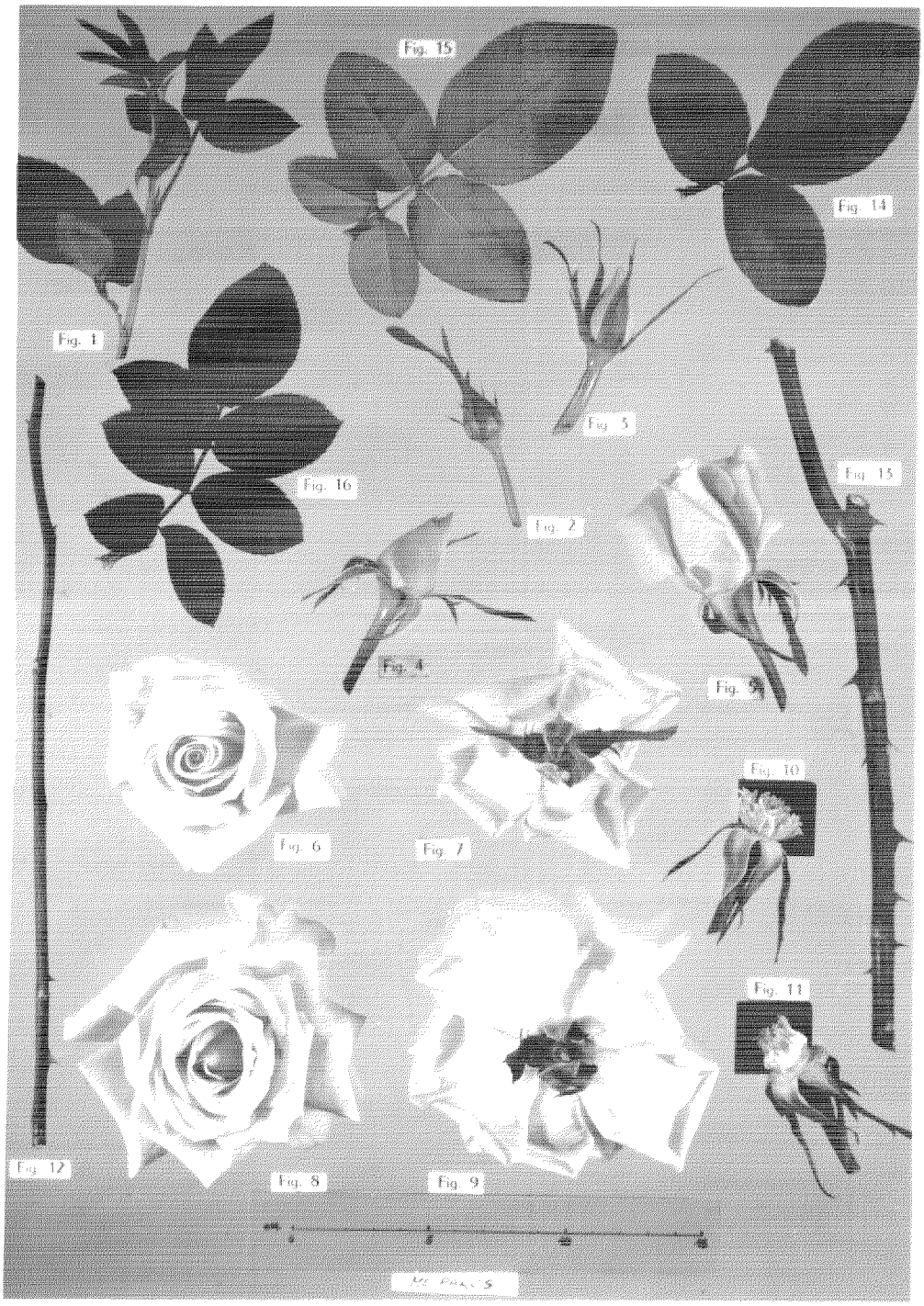

The chart used in the identification of the colors is that of The Royal Horticultural Society (R.H.S. Colour Chart). The description is based on the observation of three year-old plants during April while budded on *Rosa indicia* understock and growing in greenhouses at Le Cannet des Maures, Var, France. The coloration in common terms precedes reference to the chart in some instances.

Class: Hybrid Tea.

Plant:

*Height.*—When plants are pruned to a height of 0.85 m., floral stems of approximately 60 to 70 cm. in length commonly are formed.

*Habit.—Erect.*

Branches:

*Color.*—Young stems: Yellow-Green Group 144A, and lightly suffused with reddish coloration. Adult wood: Green Group 137A.

*Thorns.*—size: medium. Quantity: numerous. Color: reddish to brown (near Greyed-Red Group 178B).

Leaves:

*Stipules.*—Adnate, pectinate, narrow and linear.

*Petioles.*—Upper surface: striped reddish on young foliage, and dark green (commonly between Green Group 138A and 138B), on adult foliage with a few glandular edges. Under surface: light green with a few glandular edges.

*Leaflets.*—Number: 3, 5 (most often), and 7. Shape: elliptic. Size: average to large. Serration: single and regular (as illustrated). Texture: consistent. General appearance: dense, dark green, and glossy. Color (young foliage): upper surface: dark green, near Yellow-Green Group 147A and suffused with reddish-brown. under surface: dark green, near Yellow-Green Group 147A and suffused with reddish-brown. Color (adult foliage): upper surface: near Green Group 136A. under surface: near Yellow-Green Group 148C.

Inflorescence:

*Number of flowers.*—Usually one to three per stem.

*Peduncle.*—Medium green in coloration (Green Group 138B), relatively strong, smooth, and typically without prickles, and the length is approximately 11 cm. on average.

*Sepals.*—Upper surface: tomentose, and greenish (Greyed-Green Group 194B) in coloration. Under surface: medium green (commonly between Green Group 138A and 138B) in coloration and with a few extensions. Configuration: long and slender (as illustrated).

*Buds.*—Shape: conical. Length: approximately 3.5 cm. on average. Size: medium. Color upon opening: upper surface: near Red Group 37C and lightly suffused with Yellow Group 4D at the base of the petal. under surface: near Red Group 37C and lightly suffused with Yellow Group 4D at the base of the petal with the external petals being light green.

*Flower.*—Shape: elongated cup-shaped with parallel sides. Diameter: approximately 13 cm. on average. Color (when opening begins): upper surface: near Red Group 49B. under surface: near Red Group 49C. Color (when blooming): upper surface: near Red Group 49C. under surface: near Red Group 49C and Yellow Group 5D towards the base. Color (at end of opening): upper surface: near Red Group 49C. under surface: near Red Group 49C and Yellow Group 5D towards the base. Fragrance: strong and relatively stable. Lasting quality: approximately 7 days as a cut flower in a vase and while on the plant. Petal number: approximately 45 on average. Petal shape: rounded with reflexed edges. Petal drop: good with the petals commonly detaching cleanly. Stamen number: approximately 110 on average. Anthers: golden yellow in coloration. Filaments: yellowish in coloration. Pistils: approximately 130 on average. Stigmas: yellowish in coloration. Styles: pinkish-yellow in coloration. Receptacle: medium green, smooth, and in longitudinal section in the shape of a pitcher. Hips: present, but have not been studied in detail to date since this is considered to be primarily a cut-flower variety.

Development:

*Vegetation.*—Vigorous.

*Blooming.*—Abundant with approximately 140 to 180 blooms/m.$^2$/year commonly being formed.

*Resistance to diseases.*—Very good, particulary with respect to powdery mildew.

I claim:

1. A new and distinct variety of Hybrid Tea rose plant characterized by the following combination of characteristics:

(a) forms attractive long-lasting fragrant pink blossoms, (b) exhibits a vigorous erect growth habit, (c) forms attractive dark green and glossy foliage, (d) exhibits good disease resistance, and (e) is particularly well suited for cut flower production under greenhouse growing conditions;

substantially as herein shown and described.

* * * * *